United States Patent [19]

Rodgers

[11] Patent Number: 4,958,644
[45] Date of Patent: Sep. 25, 1990

[54] APPARATUS TO DISCOURAGE SUPINE SLEEP

[76] Inventor: David L. Rodgers, One Daniel Burnham Ct., San Francisco, Calif. 94109

[21] Appl. No.: 271,565

[22] Filed: Nov. 15, 1988

[51] Int. Cl.$^5$ .............................................. A61F 39/00
[52] U.S. Cl. .................................................... 128/871
[58] Field of Search .................. 128/62 R, 63, 64, 65, 128/871, 846, 848, 90, 91 R, 91 A; 2/114, 44–46

[56] References Cited

U.S. PATENT DOCUMENTS

| | | | |
|---|---|---|---|
| 132,500 | 10/1872 | Sullivan | 128/871 |
| 663,825 | 12/1900 | Wilson | 128/871 |
| 663,825 | 12/1990 | Wilson | 128/871 |
| 675,017 | 5/1901 | Roush | 128/871 |
| 794,160 | 7/1905 | Breslin | 128/871 |
| 852,638 | 5/1907 | Thomas | 128/871 |
| 876,491 | 1/1908 | Rohwer | 128/871 |
| 898,379 | 9/1908 | Liebhardt | 128/871 |
| 1,325,500 | 10/1872 | Sullivan | 128/871 |
| 2,304,235 | 6/1941 | Boots | 2/114 |
| 2,704,067 | 3/1955 | Mosses | 128/91 A |
| 2,837,088 | 6/1958 | Moses | 128/91 A |
| 3,307,537 | 3/1967 | Simon | 128/90 |
| 3,485,241 | 12/1969 | Polley | 2/114 |
| 3,485,241 | 12/1969 | Polley | 128/135 |
| 3,689,939 | 9/1972 | Taylor | 2/114 |

FOREIGN PATENT DOCUMENTS 0006425 7/1879 Fed. Rep. of Germany ...... 128/871

Primary Examiner—Robert A. Hafer
Assistant Examiner—Michael Brown
Attorney, Agent, or Firm—Townsend and Townsend

[57] ABSTRACT

An apparatus and method are provided for discouraging supine sleep, such as to avoid sleep apnea or snoring. A support device is provided, preferably with strap-like attachments, to maintain the wearable apparatus in an effective position adjacent to the back of the sleeper. A plurality of prods are positioned on the support device in a two-dimensional array. The sharpness of the prods, as felt by the sleeper, is adjustable, such as by adjusting the surface area, thickness or compressibility of material surrounding the prods, or modifying or coating the prod points. Sharpness is adjusted to either cause a supine sleeper to shift to a non-supine position, or to cause sufficient, preferably non-awakening, arousal to maintain respiration and/or to avoid snoring.

12 Claims, 2 Drawing Sheets

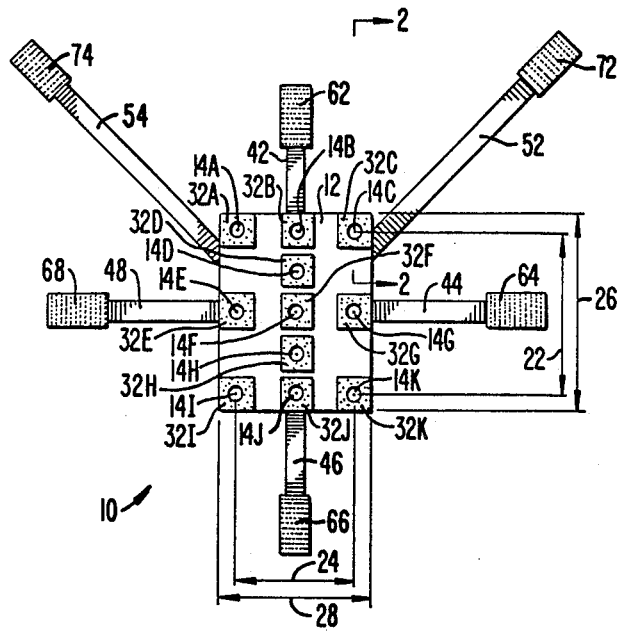
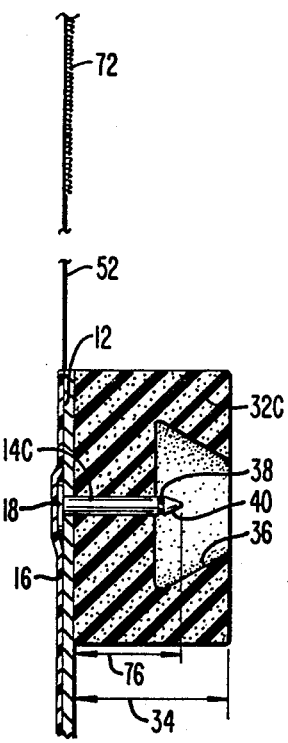
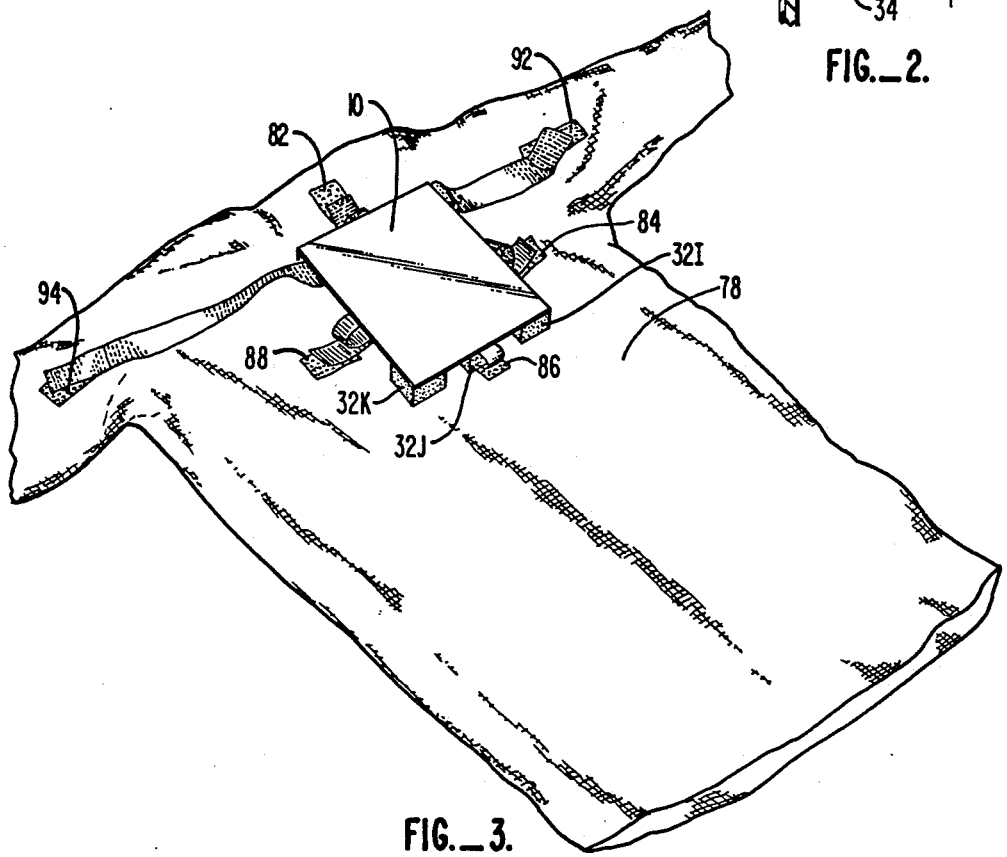
FIG._1.
FIG._2.
FIG._3.

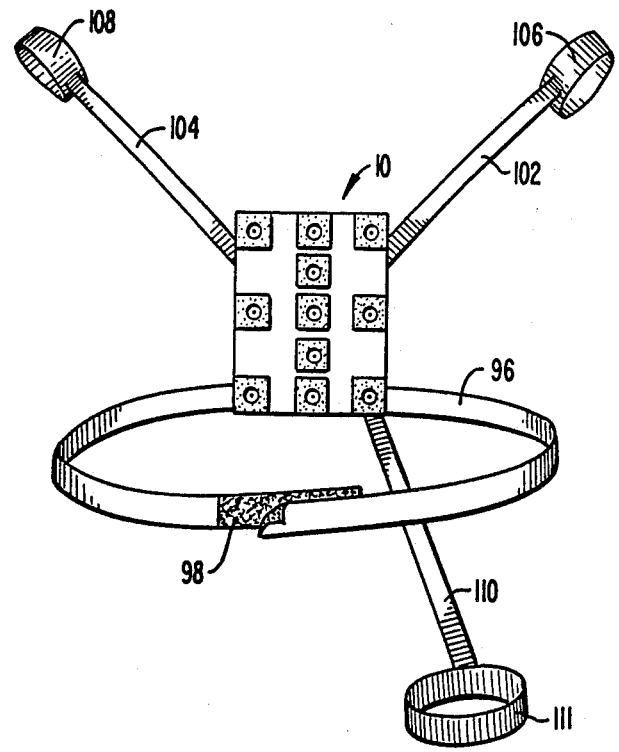
FIG._4.

4,958,644

APPARATUS TO DISCOURAGE SUPINE SLEEP

FIELD OF THE INVENTION

The present invention is directed to an apparatus and method for discouraging supine sleep and, in particular, to a wearable apparatus for causing sufficient arousal of a sleeper to maintain respiration and/or abate snoring.

BACKGROUND OF THE INVENTION

A number of undesirable or dangerous conditions are associated with particular sleep postures such as a supine sleep posture. One such condition is sleep apnea, i.e., interruption of respiration causing a decrease in blood oxygen levels and if unattended, causing death. Another such condition is snoring. Both such conditions are associated with supine sleep i.e., sleep lying on one's back, and are believed by many researchers to be particularly associated with deeper sleep.

Several types of apparatus have been previously suggested for treating or attending to such conditions. Some approaches, e.g., as described in U.S. Pat. No. 3,485,241, issued Dec. 23 1969, to Polley and U.S. Pat. No. 132,500, issued Oct. 22, 1872, to Sullivan, include protruding devices which act as physical barriers to turning on one s back. Other approaches including those described in U.S. Pat. No. 2,304,235, issued Dec. 8, 1942, to Boots, U.S. Pat. No. 898,379, issued Sept. 8, 1908, to Liebhardt, U.S. Pat. No. 876,491, issued Jan. 14, 1908, to Rohwer, and U.S. Pat. No. 663,825, issued Dec. 11, 1900, to Wilson, disclose ball-like or prodding devices disposed at a single position near the back of a sleeper. Experience with a variety of devices indicates that there is a tendency during sleep to place a wearable device in an ineffective position, where possible, in order to achieve supine sleep. For example, a device can be positioned under or below the level of the scapula so that the sleeper rests on his scapula instead of the device. Experience with single-prod devices indicates that effectiveness is defeated when the relatively small surface area of contact of the device becomes positioned during sleep in a relatively ineffective or insensitive area of the back of a sleeper, such as near the shoulder blade or hip.

Other approaches, such as described in U.S. Pat. No. 675,017, issued May 28, 1901, to Roush and German Patent No. 6425, issued July 25, 1879, to Kollosser, disclose devices with more than one contact device in a linear configuration. Experience with a linear configuration has also shown its susceptibility to placement in an ineffective position during sleep.

Previous devices generally approach the problem from the viewpoint that supine sleep must be prevented and show no awareness that, in addition to preventing supine sleep, undesired consequences thereof can be avoided using a device which can operate during supine sleep. In accordance with this belief, previous approaches were directed to producing complete awakening of a sleeper if the sleeper assumed a supine position and thus prevented an uninterrupted full night's sleep. Further consistent with the previous approaches, the prior devices did not provide for adjusting the degree of sharpness of the device with respect to the sleeper (i.e., the sharpness as felt by the sleeper), and thus did not include apparatus or methods for accommodating sleepers with varying weights sensitivities depth of sleep, and the like.

Accordingly, there is a need for a device with sufficient contact area to assure contact with sensitive regions of a sleeper, which does not require absolute prevention of supine sleep or full awakening of a supine sleeper, and of a method for adjusting an arousal device to suit the needs and circumstances of individual sleepers.

SUMMARY OF THE INVENTION

The present invention includes an apparatus having a number of prods and a way for controlling the degree of sharpness which is felt by a sleeper. The degree of sharpness is controlled so that it is sufficiently high to discourage supine sleep (i.e., to either cause the sleeper to assume a non-supine position or to at least provide enough arousal to prevent sleep apnea and/or snoring). The degree of sharpness is also controlled so that it is sufficiently low that skin penetration is substantially avoided, and so that full awakening (i.e., so as to cause interruption of a full night's sleep) is reduced, and arousal tends to be of a gradual nature.

A device is disclosed which includes a number of aspects contributing to control of the degree of sharpness as felt by a sleeper. The prods are at least partially surrounded by a compressible material, such as foam, and the surface area, thickness (with respect to the points) and/or compressibility of the material can be used to adjust sharpness. Sharpness is also affected by the points of the prods themselves, which can be selectively somewhat dulled, such as by use of a plastic coating. The number of prods also affects the sharpness as perceived by the sleeper, since distribution of a given weight over a larger number of prods produces a lower effective pressure per prod. Thus, the invention includes providing enough prods so that they cannot be readily avoided, but not so many that weight distribution results in an insufficiently-arousing device. In one preferred embodiment, eleven prods are provided.

The invention also includes a preferred size and restraint apparatus on the device to maintain the position of the device so that it is not mispositioned in an ineffective or insensitive region. This aspect of the invention effectively overcomes the tendency of a sleeper to position a wearable device to permit supine sleep.

BRIEF DESCRIPTION OF THE DRAWINGS

FIG. 1 is a front plan view of an apparatus according to the present invention.

FIG. 2 is an enlarged, partial cross-sectional view taken along line 2-2 of FIG. 1.

FIG. 3 is a perspective view of the back of an apparatus according to the present invention positioned on a nightshirt.

FIG. 4 is a perspective view of an alternative embodiment of the present invention.

DETAILED DESCRIPTION OF THE PREFERRED EMBODIMENTS

Referring now to FIG. 1, a wearable apparatus 10 includes a support structure 12 and a plurality of pointed prods 14A-14K. As best seen in FIG. 2, the prods 14A-14K are attached to the support structure 12. In a preferred embodiment, the prods 14 are in the form of points, such as roofing nails, and are attached to the support structure 12 by being inserted through the back or outside surface of the support structure 12 and held in place by glue, or an adhesive tape, or sheet 16. In this embodiment, the head 18 of the nail 14 remains adjacent to the outside surface of the support structure 12.

The prods 14 are positioned in a two-dimensional array (i.e., such that no single straight line passes through all prods). The two-dimensional array of prods 14 define an area generally having a height 22 and a width 24. The area defined by the prods 14 is sufficiently large that, although the wearable apparatus 10 may undergo some degree of movement with respect to the sleeper at least some effective portion of the area is in contact with a sensitive portion of the sleeper's back when the sleeper is supine. In this way, the device is configured so that it cannot be entirely positioned under a protected area, such as a shoulder blade. In one embodiment of the invention, the height 22 is about 10 inches (about 25 cm) and the width 24 is about 8 inches (about 20 cm). The support structure 12, accordingly, has a height 26, preferably of about 10 inches (about 25 cm) and a width 28 of about 7.8 inches (about 20 cm).

Surrounding at least each prod 14 is a layer of foam 32 having a thickness 34. The layer of foam 32 can be attached to the support structure 12 by any known convenient method, such as gluing ultrasonic welding, sewing, and the like. As best seen in FIG. 2, a hole 36 is formed in the foam 32 in the region near the point 38 of the prod 14. Preferably, the hole 36 is somewhat undercut, such as by having a frustuconical profile, so that the hole 36 has a larger diameter in the region adjacent to the tip 38 than in the region spaced from the tip. By providing undercutting, the surface foam is encouraged to give way to weight which is applied. Attached to and extending generally radially from the support structure 12 are a plurality of straps. Preferably, four straps 42, 44, 46, and 48 extend from about the middle of each edge of the support structure 12 and are attached by, for example, adhesion using the adhesive tape or sheet 16, gluing, sewing, and the like. Additional outrigger straps 52 and 54 extend at an angle to the edges of the support structure 12. Each of the straps 42, 44, 46, 48, 52, and 54 include attachment means, such as hook and loop attachment strips. e.g., Velcro ™ strips 62, 64, 66, 68, 72, and 74. The straps are long enough so that the device is not noticed by the sleeper on his other side, yet they are short enough so that the device follows the sleeper when moving from side to side, and short enough so that they do not permit the device to be escaped. The outrigger strips 52 and 54, including attachment devices 72 and 74, have a length of about 14.5 inches (about 37 cm). The remaining straps 42, 44, 46 and 48 including the attachment strips 62, 64, 66, and 68, have a length of about 8 inches (about 20 cm).

The wearable apparatus 10 can be constructed from a number of materials. The support structure 12 can be made of any material having the requisite strength and rigidity, including, e.g., plastic, cardboard, wood, metal, and rubber. The prods are of a rigid material, such as metal or plastic, and are preferably steel roofing nails. Because of the potential for irritation provided by roofing nails, and further to assist in controlling the sharpness of the point 38, as described more fully below, a layer 40 of material, such as a hardenable flowable material, e.g. plastic, a white glue or resin glue, is preferably provided around the points 38 of the prods 14. The foam 32 is preferably a compressible material which is substantially non-irritating to the skin, such as material sold under the trade name "Reston" by the 3M Company, but less resilient foam would also be acceptable.

As noted above, it has been found important to control the degree of sharpness of the prods 14 with respect to the sleeper. By "degree of sharpness," it is meant the sharpness as perceived or felt by the sleeper which can vary depending on, among other things, the sensitivity of the sleeper, the weight of the sleeper, and other factors. When a sleeper lies on his back with the wearable apparatus 10 positioned adjacent to his back the weight of the sleeper will cause compression of the foam 32, in turn causing the point 38 of the prod 14 to extend outward through the hole 36 beyond the foam 32. At this point, the prod 38 can directly or indirectly contact the skin of the sleeper. The amount of sharpness felt by the sleeper thus depends partially on the degree to which the foam is compressed. Accordingly, one way of controlling sharpness of the prods 14 with respect to the sleeper is to control the amount of compression of the foam 32 when the sleeper lies upon the wearable apparatus 10. The amount of compression, in turn, can be controlled by varying the surface area of the foam, or by varying the effective thickness of the layer 34 with respect to the prods 14 or by controlling the compressibility of the layer 32. Preferably the surface area of the foam is varied. Referring to FIG. 1, in the depicted embodiment, only a portion of the support 12 is covered by the foam portions 32A–32K. The amount that the foam will be compressed will depend, at least in part, upon the pressure applied to the foam. The pressure is equal to the weight applied divided by the surface area. If a given amount of weight is supplied to a smaller surface area, the pressure is increased and the compression of the foam is greater. Thus, the degree of sharpness felt by the sleeper can be increased by removing portions of the foam block, such as by cutting away, to decrease the surface area of foam. The effective thickness can be adjusted by varying the thickness 34 of the foam 32 (such as by providing different thicknesses of foam, shaving or removing portions of the foam, or adding or gluing additional foam layers). The effective thickness of the layer 34 can also be adjusted by adjusting the extent of the extension 76 of the prod 14 into or through the foam 32, such as by providing shorter or longer prods 14 or by providing a device such as one or more washers (not shown), for adjusting the amount of protrusion of the prods 14 through the foam 32.

The invention also includes adjusting the sharpness, as felt by the wearer, as conditions change, such as a change in the sleeper s weight aging of the sleeper, changes in the type of bed use by the sleeper, and changes in sensitivity or depth of sleep of the sleeper.

Another way of controlling the sharpness of the prods 14 is to adjust the degree of sharpness of the point 38. Providing a layer 40 adjacent to the point 38 can effectively provide some dulling of the point 38. Additionally, the point 38 can be somewhat rounded or dulled, such as by abrading or filing, or, if a higher degree of sharpness is needed, can be sharpened, such as by grinding. The particular degree of sharpness, as felt by the supine sleeper which is desired will vary depending on the sensitivity of the sleeper, the number of points or prods over which the weight of the sleeper is distributed, the type or firmness of the bed, the normal depth of supine sleep of the sleeper, and the desired depth of sleep of the sleeper.

Because of the lack of general knowledge regarding the details of human sleep, many aspects of the problem are not understood. Without wishing to be bound by any theory, however, it is believed that the wearable apparatus 10 can provide sufficient arousal to a supine sleeper that the deeper states of sleep, such as states believed by some to be associated with sleep apnea and/or snoring, are avoided, and a less deep state of sleep is maintained so as to maintain the respiration of the sleeper and avoid sleep apnea. After some period of use, it is believed that the device "trains" the sleeper to avoid supine positions. These beliefs, though not yet established by experimentation, are consistent with observations of a sleeper wearing a device, such as that depicted in FIG. 1, in which the sleeper occasionally lies in a supine position on the device 10 for up to about 3 minutes (possibly longer), during which time regular breathing is observed to continue, even when the sleeper is a person who is normally subject to sleep apnea or interruption of breathing in a supine position. Observations have indicated that after some period of such supine sleep with regular breathing, the supine sleeper will typically assume a non-supine posture.

Although the mechanisms of sleep are not well understood, it is believed on the basis of observation, that the degree of sharpness felt by a sleeper has some effect on whether the sleeper tends to lie for some periods of time in a supine position on the wearable apparatus or tends to shift to a new position. Accordingly, the present invention also includes adjusting the sharpness in order to promote either shifting to a new posture or to permit lying for some periods in a supine position on the wearable apparatus (while maintaining respiration).

As noted above, it is also important that the wearable apparatus 10 be maintained in a position adjacent to the back of the sleeper. The device should be light enough that it readily moves with the sleeper and/or nightshirt. As best seen in FIG. 3, one method of maintaining the device 10 is by using the straps 42-54 to attach the device 10 to the outside or exterior surface of a nightshirt 78. In this manner of attachment, attachment devices 82, 84, 86, 88, 92, and 94, corresponding to wearable apparatus attachment devices 62, 64, 66 68, 72, and 74, respectively, such as Velcro TM patches, are attached to the exterior surface of the back portion of the nightshirt 78, e.g., by sewing or adhesion. When attached in this manner, the wearable device 10 is maintained in an effective position, i.e., adjacent to sensitive portions of the sleeper's skin. This maintenance of the position of the device is, in turn, related to maintenance of the position of the nightshirt. Typically, the nightshirt will be held in position by the shoulder and/or hip of the sleeper.

As will be apparent from FIG. 3, the prods 14, although adjacent to the sleeper s skin, are separated therefrom by the fabric of the nightshirt. Thus, in non-supine sleep positions, the prods do not necessarily directly contact the sleeper s skin but, rather, will provide for contact through the fabric of the nightshirt 78. In this manner, the sleeper is typically substantially unaware of the device when in non-supine positions.

An alternative embodiment is depicted in FIG. 4 which, although wearable either over or under a nightshirt, can also be used without wearing a nightshirt or other garment. In the embodiment depicted in FIG. 4, a waist strap 96 is attached to the wearable apparatus 10 to be worn in a belt-like fashion, and is attachable and/or adjustable using, for example, Velcro TM strips 98, belt-type buckles (not shown), or with a provision for tying (not shown). Outrigger straps 102 and 104, positioned similarly to the outrigger strips 52 and 54 of the embodiment shown in FIG. 1, are attached to the wearable apparatus 10, and have rings or loops 106 and 108 at their terminal portions for encircling the upper arm. Preferably, the loops 106 and 108 are of an adjustable girth, such as by being elastic, having Velcro TM straps, buckles or tiable ends (not shown). A lower outrigger 110 can also be provided, if needed, for additionally stabilizing the position of the lower portion of the wearable apparatus 10. The lower outrigger has a loop 111 at its terminal end for encircling the upper thigh. The purpose of the lower outrigger is to avoid a tendency of the device to ride upwards, toward the head. Alternatively, a lower loop (not shown) can be configured to pass between the legs to maintain the lower portion of the wearable apparatus 10 in an effective position.

As will be apparent to those skilled in the art, a number of advantages are provided by the disclosed apparatus. The apparatus provides for avoidance of sleep apnea and/or snoring and maintenance of respiration without requiring full awakening of the sleeper such as would interfere with a full night's rest, and without requiring immediate movement to a non-supine position. The apparatus has controllable sharpness to accommodate the requirements of individual sleepers with regard to weight, sensitivity, and other factors. The apparatus has a two-dimensional areal extent and positioning devices to maintain effective portions of the device adjacent a sensitive region of the skin and to prevent placement of the device in an ineffective position.

A method of adjusting the support provided by the foam layer will now be set forth. In the described method, initial parameters, such as the number of prods, the sharpness of individual prods, the type of bed, and the compressibility of the foam are first selected and provided. Foam of the desired thickness is provided as described above. The device in this form is used by an adult sleeper during sleep, with provisions for sufficient monitoring or supervision to avoid sleep apnea during the adjustment process. If indications of the undesired conditions, such as sleep apnea or snoring, are found, the surface area of the foam is reduced, as described above and the process is repeated until the resulting surface area is such that the device is operative to either maintain respiration during supine sleep or cause shifting to a non-supine position. In one particular instance, a surface area of foam of about 33 square inches (about 200 $cm^2$), with a thickness 34 of foam of about 1 inch (about 2.5 cm) was found to be effective. In another instance, a device with one-half inch foam and shorter nails or prods and having a foam surface area of about 63 square inches (about 400 $cm^2$) is effective for the purpose of the device.

As will be apparent to those skilled in the art, a number of variations and modifications of the disclosed device can also be practiced. The various components of the wearable apparatus can be attached using other attachment devices, such as screws, bolts, welding, brazing, or can be provided in a substantially unitary or integral configuration, such as molding from plastic. Other types of foam can be used and other compressible materials, in addition to foam, can be used, such as fabric, rubber, and the like. The foam can be provided in a form to assist in the above-described adjustment process, such as by providing lines to indicate portions that can be cut away, or by providing easily-removable portions such as by use of perforations. The compressible materials can be of adjustable compressibility, such as by using an inflatable or pressurizable elastic membrane. Undercut configurations, other than frustuconical, can be used, such as ledge or lip-like undercutting. The support structure can be provided with reinforcing rods or bars. The wearable apparatus can be configured for attaching on the inside of a nightshirt, rather than the exterior of a nightshirt. The wearable apparatus can be configured for attachment to the top portion of pajamas, in which case, a lower outrigger may be used to prevent riding of the device towards the head. Attachment apparatus, other than Velcro TM, such as snaps, ties, or elastic straps, can be used, and the wearable apparatus can be attached without the use of straps, such as by sewing, adhesion, snaps, and the like. The device can be positioned to discourage other sleeping postures, such as by positioning on a side surface or a front surface, as might be used to avoid certain sleeping postures during recovery from injury, surgery, and the like.

Although the present invention has been disclosed with reference to a number of embodiments, other variations and modifications are included within the spirit and scope of the invention, as limited only by the appended claims.

What is claimed is:

1. An apparatus usable for preventing interruption of a sleeper's respiration, comprising:
   a support structure;
   a plurality of pointed prods, attached to said support structure to position said plurality of prods in a two-dimensional array to permit contact of a plurality of said prods with the sleeper over an area said two-dimensional array defining; wherein said means for controlling the degree of sharpness comprises a layer of compressible material substantially surrounding at least a portion of each said plurality of pointed prod; and said layer is undercut at least in a region adjacent to one of said plurality of pointed prods, said one prod having a tip, said layer including a region adjacent said tip and a region spaced from said tip, said undercut region providing a hole having a frustoconical profile with a larger diameter in the region adjacent the tip than in the region spaced from the tip.

*2. An apparatus, as claimed in claim 1, wherein:
   said layer includes a plurality of openings wherein each of said plurality of openings is substantially aligned with a corresponding one of said plurality of pointed prods.

3. An apparatus, as claimed in claim 1, wherein said means for controlling the degree of sharpness comprises:
   means for at least partially dulling the point of each of said plurality of pointed prods, while maintaining a point at each of said plurality of prods.

4. An apparatus, as claimed in claim 3, wherein said means for partially dulling comprises:
   a substantially solid layer formed adjacent to the point of at least one of said plurality of pointed prods.

5. An apparatus, as claimed in claim 1, further comprising:
   means for positioning said support structure with respect to the sleeper.

6. An apparatus, as claimed in claim 5, wherein said means for positioning includes at least one strap operatively connected to said support structure.

7. An apparatus, as claimed in claim 1, further comprising:
   means for positioning said support structure with respect to the sleeper such that at least a portion of said prod area is maintained substantially adjacent to the back of the sleeper.

8. An apparatus usable for discouraging supine sleep of a sleeper, comprising:
   a support structure; and
   a plurality of pointed prods attached to said support structure and distributed in a two-dimensional array to permit contact of a plurality of said prods with the sleeper over an area, said two-dimensional array defining a prod area having a width and a height;
   a layer of compressible foam substantially surrounding each of said plurality of pointed prods, wherein said layer includes a plurality of openings, said openings being substantially aligned with said plurality of pointed prods, and wherein said layer is undercut in regions substantially adjacent to said plurality of pointed prods.

9. An apparatus usable for discouraging supine sleep of a sleeper, comprising:
   a support board;
   a plurality of pointed prods attached to said support board and distributed in a two-dimensional array to permit contact of a plurality of said prods with the sleeper over an area, said two-dimensional array defining a prod area having a width and a height;
   a layer of compressible foam substantially surrounding each of said plurality of pointed prods, wherein said layer includes a plurality of openings, said openings being substantially aligned with said plurality of pointed prods, and wherein said layer is undercut in regions substantially adjacent to each of said plurality of pointed prods; and
   means for positioning said support structure with respect to said sleeper, such that at least a portion of said prod area is maintained adjacent the back of the sleeper.

10. An apparatus useful for preventing interruption of a sleeper's respiration, comprising:
    a support structure;
    a plurality of pointed prods, attached to said support structure in a two-dimensional array to permit contact of a plurality of said prods with the sleeper over an area, said two-dimensional array defining a prod area having a width and a height; and
    at least three straps attached to and extending from said support structure, a layer or compressible foam substantially surrounding each of said plurality of pointed prods, wherein said layer includes a plurality of openings being substantially aligned with said plurality of pointed prods, and wherein said layer is undercut in regions substantially adjacent to each of said plurality of pointed prods.

11. An apparatus, as claimed in claim 10, wherein said straps comprise means for attachment to sleepwear.

12. An apparatus, as claimed in claim 10, wherein said straps comprise means for encirclement of a portion of the sleeper's body, said straps including at least a first strap for encircling the sleeper's waist and at least a second separate strap for encircling a shoulder of the sleeper.

* * * * *